United States Patent [19]

Harris

[11] Patent Number: 4,501,742

[45] Date of Patent: Feb. 26, 1985

[54] INSECTICIDAL 3-FORMYL-2-NITROMETHYLENE-2H-1,3-THIAZINE

[75] Inventor: Martin Harris, Sittingbourne, England

[73] Assignee: Shell Oil Company, Houston, Tex.

[21] Appl. No.: 578,143

[22] Filed: Feb. 8, 1984

[30] Foreign Application Priority Data

Feb. 17, 1983 [GB] United Kingdom ................ 8304387

[51] Int. Cl.³ .................... C07D 279/04; A61K 31/54

[52] U.S. Cl. ...................................... 514/226; 544/54
[58] Field of Search ......................... 544/54; 424/246

[56] References Cited

U.S. PATENT DOCUMENTS 4,052,388 10/1977 Powell .................................. 544/54

Primary Examiner—John M. Ford

[57] ABSTRACT

3-formyl-2-nitromethylene-2H-1,3-thiazine, and its use as a pesticide.

6 Claims, No Drawings

INSECTICIDAL 3-FORMYL-2-NITROMETHYLENE-2H-1,3-THIAZINE

BACKGROUND OF THE INVENTION

U.S. Pat. No. 3,993,648 discloses a class of 2-nitromethylenetetrahydro-2H-1,3-thiazine compounds having useful pesticidal activity, 2-nitromethylene-tetrahydro-2H-1,3-thiazine having particularly high pesticidal activity. U.S. Pat. No. 4,052,388 discloses that the compound 3-acetyl-2-nitromethylene-tetrahydro-2H-1,3-thiazine also has useful pesticidal activity. However, all of those compounds have disadvantages which limit their practical use: all are unstable to light and heat, and are quite soluble in water, so that they can be relatively easily removed by dew or rain from a locus to which they have been applied.

DESCRIPTION OF THE INVENTION

It now has been found that a compound closely related structurally to the art compounds is materially more stable when exposed to light and heat, and much less soluble in water, leading to greater persistence and efficacy. This compound is 3-formyl-2-nitromethylene-tetrahydro-1H-1,3-thiazine, which has the formula

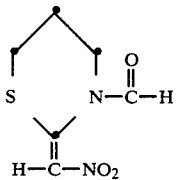

(I)

This compound is capable of existing in different geometrically isomeric forms. The invention includes both the individual isomers and mixtures of such isomers.

The invention includes also a process for the preparation of 3-formyl-2-nitromethylene-tetrahydro-2H-1,3-thiazine, which comprises reacting the compound 2-nitromethylene-tetrahydro-2H,1,3-thiazine of the formula:

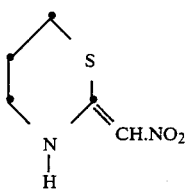

(II)

with a mixed anhydride of formic acid and an alkanoic acid containing 2 to 8 carbon atoms, for example formic acetic anhydride, in the presence of a base. The base is preferably an organic base such as a tertiary amine, for example a trialkylamine, triethylamine, being particularly preferred. The reaction is preferably carried out at a temperature of 0° C. or below, for example at a temperature from −30° C. to −10° C. The reaction is suitably carried out in an organic solvent, for example, a chlorinated hydrocarbon such as dichloromethane, or dimethylformamide.

Small quantities of water may be tolerated in the process according to the invention but it is preferably carried out under substantially anhydrous conditions.

As mentioned above, 3-formyl-2-nitromethylene-tetrahydro-2H-1,3-thiazine is of interest as a pesticide particularly against insect pests. It exhibits activity against such pests as the larval caterpillar or worm forms of insects, for example, of the genus Spodoptera and of the genus Heliothis. It is especially useful against many pests found in rice crops.

Accordingly the invention includes pesticidal compositions comprising 3-formyl-2-nitromethylene-tetrahydro-2H-1,3-thiazine together with a carrier.

It is envisaged that different isomers or mixtures of isomers may have different levels or spectra of activity and thus compositions may comprise individual isomers or mixtures of isomers. The invention further provides a method of combating pests, particular insect pests at a locus infested, or liable to infestation, by pests, which comprises applying to the locus a pesticidally effective amount of the compound or composition according to the present invention. An especially preferred locus is a paddy field bearing rice crops.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating pesticidal compositions may be used. Preferably compositions according to the invention contain 0.5 to 95% by weight of active ingredient.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montomorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example kerosine and light mineral oils; chlorinated hydrocarbons, for example carbon tetrachloride, perchloroethylene and trichloroethane. Mixtures of different liquids are often suitable.

Agricultural compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 10-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise'-like consistency.

A composition of the invention may also contain other ingredients, for example, one or more other compounds possessing pesticidal, herbicidal or fungicidal properties, or attractants, for example pheromones or food ingredients, for use in baits and trap formulations.

It has also been found that the thermal stability of the compound and composition of the invention may be improved by the addition of stabilizing amounts, usually 10-100% w based on the compound, of certain organo nitrogen compounds such as urea, dialkylureas, thiourea or guanidine salts or alkali metal salts of weak acids such as bicarbonates, acetates or benzoates.

The invention is illustrated further in the following Examples.

EXAMPLE 1

Preparation of 3-formyl-2-nitromethylene-tetrahydro-2H-1,3-thiazine

Triethylamine (5.2 ml) was added to a stirred solution of 2-nitromethylene-tetrahydro-2H-1,3-thiazine (3.2 g) in dry dichloromethane (30 ml) at ambient temperature under nitrogen.

The solution was then cooled to $-20°$ C. and formic acetic anhydride (5.6 g) in dry dichloromethane (30 ml) was added dropwise with stirring. The temperature of the solution was then allowed to rise to $0°$ C. with continued stirring over a period of 30 minutes. The reaction mixture was then poured into a mixture of ice and 2M HCl (10 ml). The organic layer was separated, washed with 2M HCl (50 ml) followed by water, and dried ($MgSO_4$). The solvent was then removed under reduced pressure and the residue was recrystallised from chloroform to yield the desired product as a yellow crystalline solid m.p. $138°-140°$ C.

Analysis Calculated for $C_6H_8O_3N_2S$: C, 38.3%; H, 4.3%; N, 14.9% Found: C, 38.5%; H, 4.3%; N, 14.5%.

EXAMPLE 2

Pesticidal Activity

The pesticidal activity of the compound of the invention was assessed against the following insect pests.

*Spodoptera littoralis:* (S.l.)
*Aedes aegypti:* (A.a.)
*Musca domestica:* (M.d.)
*Aphis fabae:* (A.f.)

The test methods employed for each species appear below; in each test, unless otherwise stated, a 0.2% solution or suspension of the test compound in 16.7% acetone in water containing 0.04% Triton X-100 (Trade Mark) was sprayed onto the test species; controls were sprayed with a control solution of water, acetone and Triton X-100 in the same proportions. The tests were all conducted under normal insectary conditions $23°$ C.$\pm 2°$ C. (fluctuating light and humidity).

(i) *Spodoptera littoralis* (S.l.)

Second instar larvae were used in the tests. Each test solution and the control solution was sprayed onto a separate petri dish containing a nutrious diet on which the *Spodoptera littoralis* larvae had been reared.

When the spray deposit had dried each dish was infested with 10 2nd instar larvae. Mortality assessments were made 1 and 7 days after spraying and the percentage mortality calculated.

(ii) *Aedes aegypti* (A.a.)

Early 4th instar larvae were used in the tests. Test solutions were made up to 3 ppm of active ingredient in water containing 0.04% Triton X-100 (Trade Mark); acetone was initially present to aid solution, but was subsequently allowed to evaporate off.

Ten early 4th instar larvae were placed in 100 ml of the test solution. After 48 hours, larval mortality (as a percentage) was recorded.

Any surviving larvae were then fed with a small quantity of animal feed pellets and the final percentage mortality of adults and pupae made when all the larvae had either pupated and turned into adults, or died.

(iii) *Musca domestica* (M.d.)

Batches of ten 2 to 3 day old milk-fed adult female house-flies (*Musca domestica*) anaesthetized using carbon dioxide were placed on petri dishes lined with filter paper. The dishes were sprayed with the test formulations using a spray machine operating on a logarithmic dilution principle. The flies were subsequently retained in the petri dishes and were fed with a dilute mild solution which was dripped down the side of the petri dish and absorbed onto the filter paper. Mortality was assessed after 24 hours.

(iv) *Aphis fabae* (A.f.)

Tests were carried out on adult black bean aphids (*Aphis fabae*). Pairs of broad bean leaves on filter paper in petri dishes were sprayed side by side with uncounted quantities of aphids in small gauze-covered containers. After passing through the spray the aphids were tipped onto the leaves and lids were placed on the petri dishes. Mortality was assessed after 24 hours.

The results of these tests are shown in Table I below in which the test species are identified by the initials noted above and the activity of the compound is expressed in terms of the percentage mortality:

A denotes 90–100% mortality,
B denotes 50–80% mortality,
C denotes 0–40% mortality.

TABLE I

| Insecticidal Activity | | | | | |
|---|---|---|---|---|---|
| S.l. | | A.a. | | | |
| 1 day | 7 days | 2 days | Final | M.d. | A.f. |
| A | A | A | A | A | A |

EXAMPLE 3

Measurement of Persistence

This test is designed to measure the persistence of compounds under conditions approximately field conditions.

Third instar larvae of the corn earworm, *Heliothis zea*, were used as test species. Each test compound was dissolved in 1.0 ml of a 1:1 mixture of xylene:acetone and 0.1 ml of surfactant was added. Tap water was added to bring the volume up to 10.0 ml. This solution was then diluted with water to produce a spray dosage equivalent to 100 g active ingredient per hectare.

Pot-grown cotton plants 15 to 20 cms tall were trimmed to 2 leaves, and sprayed using a travelling spray nozzle. 10 plants were used for each treatment. After spraying, two plants were immediately infested with 5 larvae, and the remaining plants were stored in a chamber provided with banks of electric light approximating sunlight. Two plants were subsequently removed from the chamber 1, 2, 4 and 7 days after spraying, and infested with 5 larvae. Glass globes were placed over the plants to prevent larvae escaping. 48 hours after infestation, the percentage mortality of the larvae was measured. The results obtained are given in Table II below. Compounds Tested:

A: 3-formyl-2-nitromethylene-tetrahydro-2H-1,3-thiazine (compound of the present invention),
B: 2-nitromethylene-tetrahydro-2H-1,3-thiazine (compound of U.S. Pat. No. 3,993,648),
C: 3-acetyl-2-nitromethylene-tetrahydro-2H-1,3-thiazine (compound of U.S. Pat. No. 4,052,388).

TABLE II

| Compound Tested | 48 Hour Percentage Mortality Days after Spraying | | | | |
|---|---|---|---|---|---|
| | 0 | 1 | 2 | 4 | 7 |
| A | 100 | 100 | 100 | 100 | 100 |
| B | 100 | 55 | 0 | 0 | 0 |
| C | 100 | 100 | 50 | 0 | 0 |

The results show that all compounds tested killed all the larvae infesting the test plants immediately after spraying. However, 1 day after spraying, the deposit on the plants treated with prior art compound B only killed 55% of the larvae; 2 days after spraying, compound B was completely inactive. 2 days after spraying, the deposit on the plants treated with prior art compound C only killed 50% of the larvae, and compound C was completely inactive 4 days after spraying. In contrast, the compound according to the present invention still killed all the larvae infesting plants 7 days after spraying.

I claim:

1. 3-formyl-2-nitromethylene-tetrahydro-2H-1,3-thiazine.

2. A process for the preparation of 3-formyl-2-nitromethylene-tetrahydro-2H-1,3-thiazine which comprises reacting 2-nitromethylene-tetrahydro-2H-1,3-thiazine with an anhydride of formic acid and an alkanoic acid containing 2 to 8 carbon atoms in the presence of a base.

3. A insecticidal composition comprising an insecticidally effective amount of the compound of claim 1 together with a carrier.

4. A composition according to claim 3 which also contains a surface-active ingredient as an essential component.

5. A composition according to claim 3 which also contains from about 10% to about 100% by weight of the thiazine of a material selected from urea, dialkylureas, thiourea, guanidine salts and alkali metal bicarbonates, acetates and benzoates, to stabilize the thiazine against the effect of heat.

6. A method of combating insects at a locus which comprises applying to the locus an insecticidally effective amount of the compound of claim 1 or a composition of claim 3.

* * * * *